Dec. 11, 1956 E. S. BOERNER Plant Pat. 1,535
ROSE PLANT
Filed Jan. 13, 1956
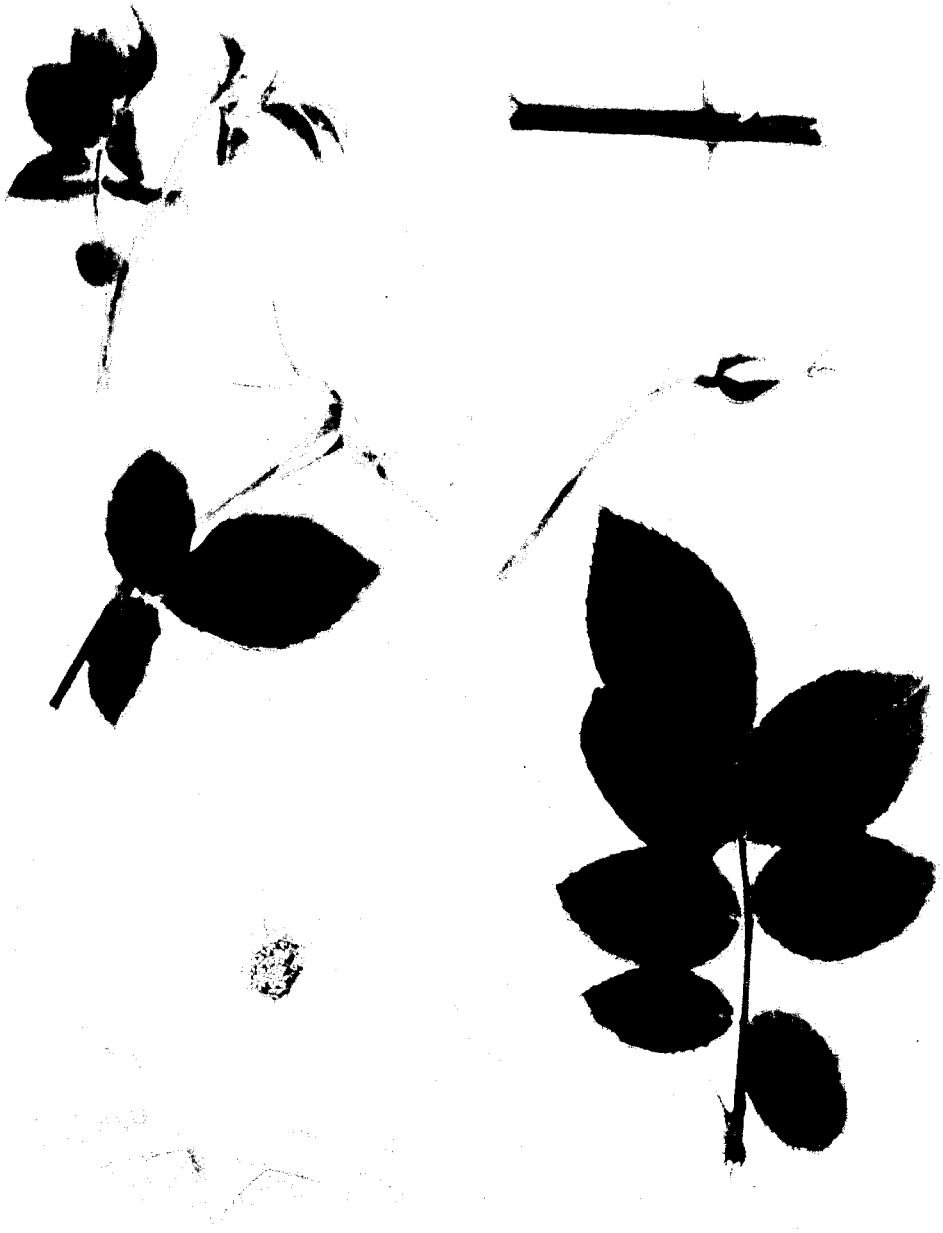
Inventor.
E. S. Boerner
By: Robb & Robb
Attorneys.

United States Patent Office

Plant Pat. 1,535
Patented Dec. 11, 1956

1,535

ROSE PLANT

Eugene S. Boerner, Newark, N. Y., assignor to Jackson & Perkins Company, Newark, N. Y., a corporation of New York Application January 13, 1956, Serial No. 559,084

1 Claim. (Cl. 47—61)

The present invention relates to a new and distinct variety of rose plant of the large-flowered polyantha class, which was originated by me by crossing the variety "Yellow Pinocchio" (Plant Patent No. 992) with the variety "Fashion" (Plant Patent No. 789).

The primary objective of this breeding was to produce a new rose variety which is more hardy and which bears deeper colored flowers than those of the "Pinocchio" type. This objective was fully achieved, as evidenced by the following characteristics which are especially outstanding in my new variety:

(1) The floriferousness of the new variety;

(2) The improved hardiness which is especially desirable in a floribunda rose;

(3) The long-lasting quality of the flowers as cut flowers; and (4) The distinctive Maize Yellow general color tonality of the buds which open slowly and gradually to mature flowers of Maize Yellow lightly overcast with Buff Yellow general color tonality.

Asexual reproduction of my new variety by budding, as performed at Newark, New York, and also at Pleasanton, California, shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Robert Ridgway's Color Standards and Nomenclature:

Parentage: Seedling.
*Seed parent.*—"Yellow Pinocchio."
*Pollen parent.*—"Fashion."
Classification.
*Botanic.*—Large-flowered polyantha.
*Commercial.*—Floribunda.

FLOWER (Observations made from specimens grown in a greenhouse at Newark, New York, toward the middle of August and in the early morning).

Blooming habit: Recurrent—continuous.
Bud:
*Size.*—Medium.
*Form.*—Ovoid; is not affected by wet or hot weather.
*Color.*—When sepals first divide—Coral Pink, Plate 13. When petals begin to unfurl—Light Orange Yellow, Plate 3, with edges of Orient Pink, Plate 2. When half-blown: Inside of petals—Maize Yellow, Plate 4; reverse of petals—Buff Yellow, Plate 4, lightly overcast with Baryta Yellow, Plate 4.
*Sepals.*—Branched; curl back when petals begin to unfurl. Color: Inside—Kildare Green, Plate 31; outside—Rinnemann's Green, Plate 18.
*Calyx.*—Color—Cress Green, Plate 31. Shape—funnel. Size—small. Aspect—smooth. Odor when rubbed—none.
*Peduncle.*—Length — medium. Aspect — smooth. Strength—erect; slender. Color—Oil Green, Plate 5.
*Opening.*—Opens up well; is not affected by adverse weather conditions.
Bloom:
*Size.*—Large. Average size when fully expanded—3½ inches.
*Borne.*—Several together and in irregular clusters.
*Stems.*—Medium length; strong.
*Form (when first open).*—Open. Permanence—Retains its form to the end, but outer petals curl back.
*Petalage.*—Double (full but open center). Number of petals under normal conditions—From 40 to 45.
*Color.*—Center of flower—Orange Buff, Plate 3, lightly overcast with Light Orange Yellow, Plate 3. Outer petals—Maize Yellow, Plate 4. Base of petals (aiglet)—Picric Yellow, Plate 4. Inside of petals—Maize Yellow, Plate 4, lightly overcast with Buff Yellow, Plate 4. Reverse of petals—Cream Color, Plate 16. General tonality from a distance—Maize Yellow, Plate 4, lightly overcast with Buff Yellow, Plate 4.
*Discoloration.*—General tonality at end of first day—Maize Yellow, Plate 4, overcast with Buff Yellow, Plate 4. Second day—Maize Yellow, Plate 4, lightly overcast with Buff Yellow, Plate 4. Third day—Maize Yellow, Plate 4.
Petals:
*Texture.*—Leathery; is not affected by wet or hot weather. Inside—satiny; outside—shiny.
*Form.*—Oval.
*Arrangement.*—Informal (with "rags" in center).
*Petaloids in center.*—Few; large.
*Persistence.*—Drop off cleanly.
*Fragrance.*—Moderate. Nature—tea (average hybrid tea scent).
*Lasting quality.*—On the plant—very long; as cut flower—very long.

GENITAL ORGANS

Stamens, anthers: Medium size; few; regularly arranged around styles. Color—Capucine Orange, Plate 3.
Stamens, filaments (threads): Medium length. Color—Picric Yellow, Plate 4.
Pollen: Color—Cream Color, Plate 16.
Styles: Bunched; uneven length; medium length; thin.
Stigmas: Color—Light Orange Yellow, Plate 3.
Ovaries: Some protruding from calyx.
Hips: None.
Seeds: None.

PLANT

Form: Bush.
Growth: Vigorous; bushy.
Foliage: Compound of 5 to 7 leaflets.
*Size.*—Medium.
*Quantity.*—Abundant.
*Color.*—New foliage: Upper side—Spinach Green, Plate 5, with serrations of Bordeaux, Plate 12; under side—Oil Green, Plate 5, lightly overcast with Bordeaux, Plate 12. Old foliage: Upper side—Dark Cress Green, Plate 31; under side—Light Bice Green, Plate 17.
*Shape.*—Oval pointed.
*Texture.*—Upper side—glossy; under side—smooth.

*Ribs and veins.*—Ordinary.
*Edge.*—Serrated (saw-toothed).
*Serration.*—Single; small.
*Leaf stem.*—Color—Light Hellebore Green, Plate 17. Under side—prickly.
*Stipules.*—Medium length; bearded.

Wood:
*New wood.*—Color—Lettuce Green, Plate 5. Bark—smooth.
*Old wood.*—Color—Dark Cress Green, Plate 31. Bark—smooth.

Thorns:
*Thorns.*—Quantity: On main stalks from base—ordinary; on laterals from stalk—ordinary. Form—narrow base; medium length; straight. Color (when young)—Amaranth Purple, Plate 12. Position—irregular.

*Prickles.*—Quantity: On main stalks—none; on laterals—none.
*Short needles.*—Quantity: On main stalks—none; on laterals—none.

I claim:

A new and distinct variety of rose plant of the large-flowered polyantha class, substantially as herein shown and described, characterized particularly as to novelty by its floriferousness, its hardiness, the long-lasting quality of its flowers as cut flowers, and the distinctive Maize Yellow color of its buds which open slowly and gradually to mature flowers of a distinctive Maize Yellow lightly overcast with Buff Yellow general color tonality.

No references cited.